United States Patent [19]

Cotter

[11] 4,262,398
[45] Apr. 21, 1981

[54] CALVARIUM CAP

[76] Inventor: William L. Cotter, 533 E. Mulberry St., Watseka, Ill. 60970

[21] Appl. No.: 91,044

[22] Filed: Nov. 5, 1979

[51] Int. Cl.³ .............................................. A61N 1/00
[52] U.S. Cl. ...................................................... 27/21
[58] Field of Search ..................... 27/21; 128/163, 153, 128/89 A, 164; 2/425

[56] References Cited

U.S. PATENT DOCUMENTS

| 1,073,185 | 9/1913 | Turner | 128/153 |
| 1,587,558 | 6/1926 | Sheffield | 128/89 A |
| 1,736,515 | 11/1929 | Anderson | 128/153 |
| 2,599,523 | 6/1952 | Dorr | 128/153 |
| 3,220,081 | 11/1965 | Rector | 27/21 |

Primary Examiner—John D. Yasko
Attorney, Agent, or Firm—Hill, Van Santen, Steadman, Chiara & Simpson

[57] ABSTRACT

An elongated, eliptically shaped, piece of material with a centrally located space and eyelets attached at each end can be used to reliably retain a calvarium adjacent an associated skull.

8 Claims, 3 Drawing Figures

CALVARIUM CAP

BACKGROUND OF THE INVENTION

1. Field of the Invention

The invention pertains to mortuary related devices.

2. Prior Art

In cases where the body of a deceased is to be prepared to be viewed by family and friends where a cranial autopsy has been performed, there has been a problem with securing the calvarium to the top of the skull to insure that the calvarium will not slip away. If the calvarium should slip away from the top of the skull, there results in a noticeable indentation of the forehead of the deceased which is very undesirable.

Prior attempts to ensure that the calvarium does not slip away from the skull have included drilling additional holes in the bone structure and passing suturing material through the holes to connect the calvarium to the skull. Alternately, attempts have been made to suture the calvarium directly to the muscle tissue above the ears of the deceased.

All of the prior attempts to ensure that the calvarium does not slip away from the rest of the skull have either not resulted in a reliable enough connection between the calvarium and the skull or have taken a great deal of time to complete.

Thus, there has been a need for a reliable and inexpensive device whereby the calvarium might be quickly and securely reattached to the top of the skull.

SUMMARY OF THE INVENTION

The invention comprises a calvarium cap usable to securely and quickly reattach the calvarium to the top of the skull after a cranial autopsy has been conducted.

The inventive cap is formed from a single piece of material which has been cut so as to have a generally eliptical shape. In the center of the piece of material, a smaller elipse or oblong shaped piece of material is removed. At each end of the eliptically shaped device, an eyelet or a rivet is inserted through a hole in the material.

Suitable materials for the device include canvas, nylon, double-knit materials or rubber.

A second eyelet or rivet may be added to each end of the shaped piece of material. The use of the second eyelet at each end provides a means for adjustment. As a result the fit of the inventive cap across the calvarium can be optimized.

BRIEF DESCRIPTION OF THE PREFERRED EMBODIMENTS

Figure 1:
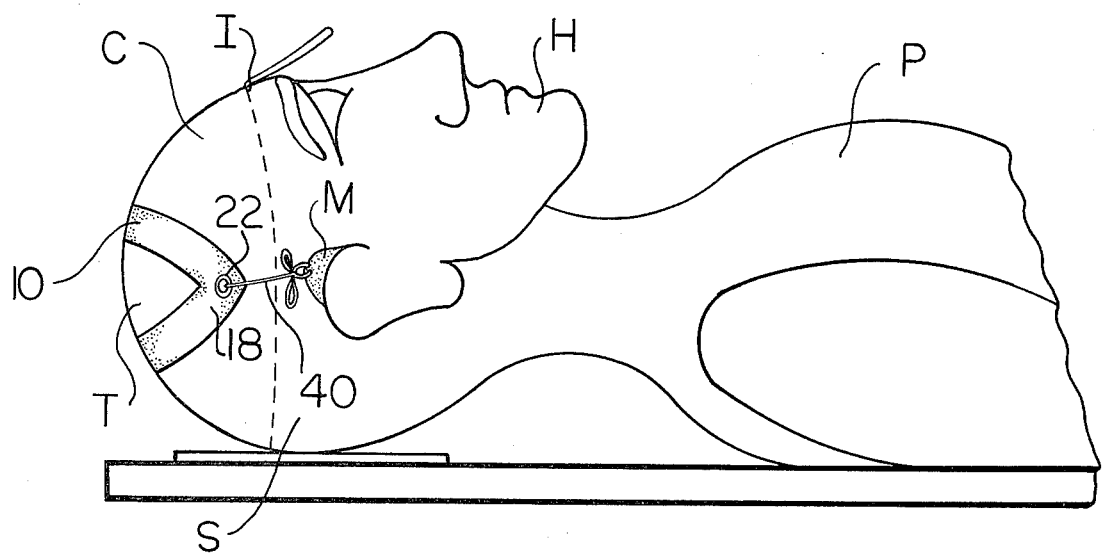
FIG. 1 is a side elevation of the inventive calvarium cap in position.
Figure 2:
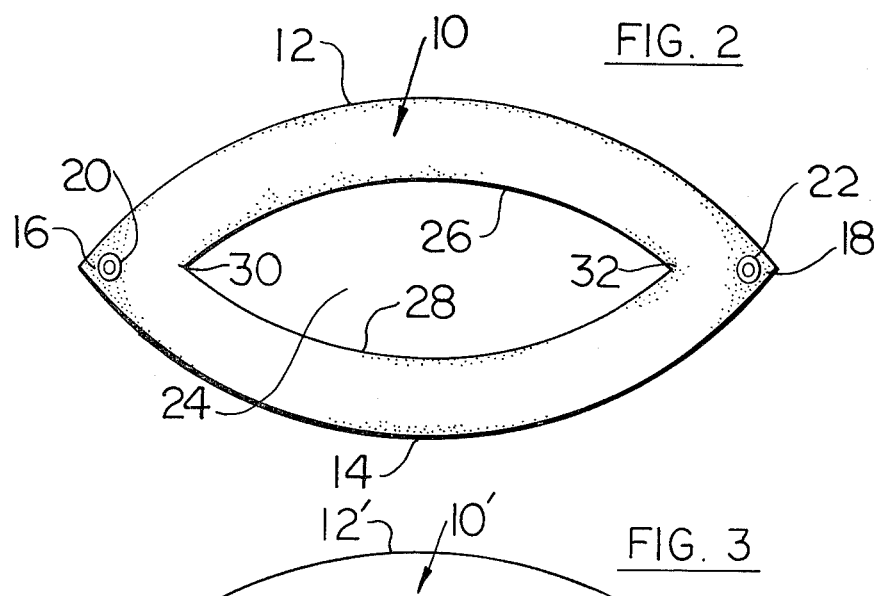
FIG. 2 is a planar top view of one inventive embodiment.
Figure 3:
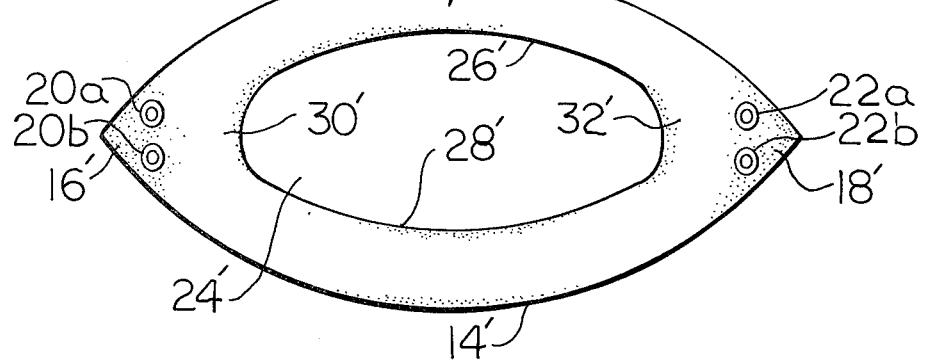
FIG. 3 is a planar top view of a second inventive embodiment.

Not by way of limitation, but by way of disclosing the best mode of practicing my invention, and by enabling one of ordinary skill to practice my invention, there are shown in FIGS. 1 through 3 two embodiments of my invention.

FIG. 1 shows the head H of a deceased person P wherein a cranial incision I has been made in the skull S in order that the calvarium C might be removed for the purpose of conducting a cranial autopsy.

In order to prepare the body of the deceased person P for final viewing, a calvarium cap 10 can be utilized to reliably and quickly reattach the calvarium C to the top of the skull S.

FIG. 2 is a planar view of the calvarium cap 10. The calvarium cap 10 is an eliptically shaped piece of material with top and bottom edges 12 and 14 which intersect at ends 16 and 18. Adjacent the end 16 a hole is made, through which is placed a metallic eyelet 20. Similarly, adjacent the end 18 a similar hole is made through which is placed a second metallic eyelet 22. The eyelets 20, 22 form a means for attaching affixed to the cap 10. A central region of the calvarium cap 10 is removed leaving an eliptically shaped space 24 having a first edge 26 and a second edge 28. The edges 26 and 28 intersect, forming a first point 30 and a second point 32.

With reference to FIG. 1, the calvarium cap 10 may be laid across the top surface T of the calvarium C and a ligature 40 may be passsed through the eyelet 22 and used to connect the end 18 of the cap 10 to the muscle tissue M, which is above the ear of the head H of the deceased P. A ligature corresponding to the ligature 40 may also be passed through the eyelet 20 and connected to the muscle tissue on the other side of the head H of the deceased P. The eliptical shape of the calvarium cap 10, along with the eliptical space 24 in the center of the cap 10 make it possible to quickly and securely reattach the calvarium C to the top of the skull S by means of the ligatures 40. Because of the shape of the calvarium cap 10, it applies forces evenly throughout the calvarium C preventing the undesirable slippage.

FIG. 3 discloses an alternate embodiment of the calvarium cap 10 which has a central space 24' with an oblong shape with two round ends 30', 32'.

FIG. 3 also includes four eyelets, 20a, b and 22a, b. Each pair of eyelets 20a, b and 22a, b is attached adjacent a respective end 16', 18'. The additional eyelet 20b, 22b incorporated at each end 16', 18' of the bandage 10' provide means for adjustment of the cap 10' with respect to the head H. A second ligature could be used at each side of the head H to connect the second eyelet 20b, 22b to adjacent muscle tissue to insure that the calvarium C is firmly held to the top of the skull S.

I have found that canvas is the preferred material to be used for the caps 10, 10' although alternate materials such as nylon, double-knit materials, aletex or rubber might also be used. The eyelets 20, 22 are preferred over just putting holes in the material of the calvarium cap 10 because of the tension applied to the material by the ligatures 40. The eyelets or rivets 20, 22 can be formed of metal, plastic or any other suitable material.

While various modifications and changes might be proposed by those skilled in the art, it should be understood that I wish to embody within the claims of the patent warranted hereon all such modifications and changes as reasonably come within my contribution to the art.

I claim as my invention:

1. A calvarium cap adapted to hold a detached calvarium against the rest of the skull comprising:
   a piece of elongated material of a generally eliptical shape,
   said piece of material has a first curved member which is joined by a second curved member to form first and second ends;

said piece of material has an elongated space in the central region thereof between said members;

said piece of material has first and second holes, of relatively small diameter, respectively adjacent said first and second ends; and first and second eyelets inserted through said first and second relatively small diameter holes with first and second ligatures attached to said first and second eyelets such that said piece of material is positionable across the top of the calvarium and said ligatures are each attachable to adjacent muscle tissue on the skull to firmly hold the calvarium against the skull.

2. The calvarium cap according to claim 1, wherein said elongated space in said central region has an eliptical shape and is bounded by first and second curved surfaces which intersect forming first and second points.

3. The calvarium cap according to claim 1, wherein said elongated space in said central region has an oblong shape with generally rounded ends.

4. The calvarium cap according to claim 1, wherein said material is a canvas material.

5. The calvarium cap according to claim 4, wherein said material is substantially equal to seven inches in length, and substantially equal to three inches in width at its widest point.

6. The calvarium cap according to claim 1 including further:

third and fourth holes, of relatively small diameter, located adjacent said first and second holes respectively;

third and fourth eyelets inserted through said third and fourth, relatively small diameter, holes and third and fourth ligatures attached thereto such that the fit of said piece of material can be further adjusted by fastening said third and fourth ligatures to adjacent muscle tissue on the skull.

7. A calvarium cap adapted to hold a previously removed calvarium against the rest of a skull comprising:

an eliptically shaped piece of canvas with an elongated opening in the center thereof;

first and second holes of relatively small diameter adjacent first and second ends of said piece of canvas;

whereby said piece of canvas can be laid across the top of the calvarium with said first and second holes on opposite sides thereof, and the calvarium can be held against the skull by said piece of canvas by connecting ligatures between said first and second holes in said piece of canvas and adjacent tissue on the skull.

8. The calvarium cap according to claim 7, including further:

first and second eyelets inserted through said first and second holes.

* * * * *